(12) United States Patent
He et al.

(10) Patent No.: US 8,097,725 B2
(45) Date of Patent: Jan. 17, 2012

(54) LUMINESCENT INDICATOR DYE AND OPTICAL SENSOR

(75) Inventors: Huarui He, Alpharetta, GA (US); Mark A. Mortellaro, Frederick, MD (US); Susanne T. Young, Norcross, GA (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 1636 days.

(21) Appl. No.: 11/003,163

(22) Filed: Dec. 3, 2004

(65) Prior Publication Data

US 2006/0121623 A1  Jun. 8, 2006

(51) Int. Cl.
*C07D 221/14* (2006.01)

(52) U.S. Cl. .......................................... 546/79; 73/435

(58) Field of Classification Search ................ 546/79; 73/435

See application file for complete search history.

(56) References Cited

U.S. PATENT DOCUMENTS

| | | |
|---|---|---|
| 5,952,491 A | 9/1999 | Leiner et al. |
| 6,001,999 A | 12/1999 | Wolfbeis et al. |
| 6,107,083 A | 8/2000 | Collins et al. |
| 6,171,866 B1 | 1/2001 | He et al. |
| 6,211,359 B1 | 4/2001 | He et al. |
| 6,214,185 B1 | 4/2001 | Offenbacher et al. |

FOREIGN PATENT DOCUMENTS

| | | |
|---|---|---|
| EP | 0 881 488 A2 | 12/1998 |
| EP | 1 081 152 A1 | 3/2001 |
| WO | WO 00/31039 | 6/2000 |
| WO | WO 00/32577 | 6/2000 |
| WO | WO 03/100083 A1 | 12/2003 |

OTHER PUBLICATIONS

Jeffery Spirior, 1994, Lifetime based optical sensing of pH . . . .*
DaFu Chi et al, Optical fibre pH senso based on immobilised indicator., 1991.*
Leiner, M.J.P., Hartmann, P., "Theory and practice in optical pH sensing", Sensors and Actuators B, 11 (1993) 281-289.
Leiner, M.J.P., "Optical sensors for in vitro blood gas analysis", Sensors and Actuators B 29 (1995) 169-173.
He, H., Mortellaro, M.A., Leiner, M.J.P., Young, S.T., Fraatz, R.J., Tusa, J.K., "A Fluorescent Chemosensor for Sodium Based on Photoinduced Electron Transfer", Anal. Chem. 2003, 75, 549-555.
He, H., Mortellaro, M.A., Leiner, M.J.P., Fraatz, R.J., Tusa, J.K., "A Fluorescent Sensor with High Selectivity and Sensitivity for Potassium in Water", J. Am. Chem. Soc. 2003, 125, 1468-1469.
Werner, T., Huber, C., Heinl, S., Kollmannsberger, M., Daub, J., Wolfbeis, O.S., "Novel optical pH-sensor based on a boradiaza-indacene derivative", Fresenius J Anal Chem (1997) 359: 150-154.
Gareis, T., Huber, C., Wolfbeis, O.S., Daub, J., "Phenol/phenolate-dependent on/off switching of the luminescence of 4, 4-difluoro-4-bora-3a,4a-diaza-s-indacenes", Chem. Commun., 1997, 1717-1718.

* cited by examiner

*Primary Examiner* — Rita Desai
(74) *Attorney, Agent, or Firm* — Dinsmore & Shohl LLP

(57) ABSTRACT

The present invention relates to a chemical compound that has applications as a luminescent indicator dye, and to an optical sensor, typically employed for determination of near-neutral pH values of aqueous samples. The optical sensor has particular application in the pH determination of body liquids such as, for example, blood, plasma and serum.

12 Claims, 3 Drawing Sheets

LUMINESCENT INDICATOR DYE AND OPTICAL SENSOR

BACKGROUND OF THE INVENTION

The present invention relates to a chemical compound that has applications as a luminescent indicator dye, and to an optical sensor, typically employed for determination of near-neutral pH values of aqueous samples. The optical sensor has particular application in the pH determination of body liquids such as, for example, blood, plasma and serum.

Measuring the pH is an essential task in many fields of science and technology, for instance in chemistry, process engineering, manufacturing and environmental analysis. A number of optical sensors for determination of pH have been proposed. Surveys with emphasis on determination and monitoring of blood pH by means of optical sensors have been given by Leiner and Wolfbeis, *Fiber Optic pH Sensors*, in CRC BOOK ON FIBER OPTIC CHEMICAL SENSORS AND BIOSENSORS (O. S. Wolfbeis ed., CRC Press Inc., Boca Raton, Fla. (1991)) and Leiner and Hartmann, *Theory and practice in optical pH sensing*, SENSORS AND ACTUATORS, B 11, 281-289 (1993).

For blood gas analysis it is essential that pH is determined very accurately. See Leiner, *Optical sensors for in vitro blood gas analysis*, SENSORS AND ACTUATORS, B 29, 169-173 (1995).

Recently, new optical sensors suitable for measurement of sodium and potassium in serum, plasma and whole blood samples have been described. The optical sensors are based on PET dyes immobilized in a hydrophilic polymer layer. See He et al., *A fluorescent chemosensor for sodium based on photoinduced electron transfer*, ANAL. CHEM. 75, 549-555 (2003); He et al., *A fluorescent sensor with high selectivity and sensitivity for potassium in water*, J. AM. CHEM. SOC. 125, 1468-1469 (2003). The "PET effect" (PET=photoinduced electron transfer) denotes the photone induced transfer of electrons from a donor to luminophoric moiety.

PET dyes sensitive to pH are known, which dyes were initially used to study luminescent PET systems (Bissel et al., *Luminescence and Charge Transfer. Part 2. Aminomethyl Anthracene Derivatives as Fluorescent PET (Photoinduced Electron Transfer) Sensors for Protons*, J. CHEM. SOC. PERKN TRANS 2, 1559-1564 (1992)) in solvents. In early studies, aliphatic and aromatic amines were suggested as the pH sensitive part (donor part) for the PET dye. The latter were attached to luminescent polycyclic aromatic compounds (acceptor part) to yield a pH sensitive PET dye. PET dyes containing amino-groups show a strong difference in luminescence intensity of protonated and deprotonated species. The donor part bound via a spacer group to the acceptor part acts as a luminescence quencher. In the protonated state no quenching of the luminescence of the electronically excited acceptor part occurs. In the deprotonated state, the PET donor group quenches the luminescence of the electronically excited acceptor part. The quenching efficiency depends on the ability of the quencher part to transfer an electron to the electronically excited acceptor part and on the ability of the electronically excited acceptor part to accept the electron.

Since the ratio of protonated and de-protonated dye species depends on both the pH (pH=−log(concentration or activity of protons)) in the vicinity of the PET donor group and the pK of the pH-sensitive chemical group of the PET donor part, luminescence intensity of the PET dye depends on pH. The pK is defined as pH at which the ratio of protonated and de-protonated dye species equals 1.

In general, the useful pH-range, i.e., the pH range, where significant changes of luminescence intensity occur is about pK+/−1.5 units.

For determination of near neutral pHs of watery samples it is therefore required that the pK of the PET donor group is near neutral (close to 7) in an aqueous environment. For determination of blood pH at 37° C. by means of an optical sensor the 37° C. pK measured by exposing the sensor to calibration solutions of different pHs, is most preferably close to 7.4+/−0.3 pH units.

Preferred amines for PET quenching are unsubstituted aliphatic amines (i.e., —$CH_2$—$NH_2$; NOT —$CH_2$—NRH or —$CH_2$—$NR_2$) and unsubstituted aromatic amines (i.e., phenyl-$NH_2$). Typical pKs of unsubstitutes aliphatic amines are near 9. Typical pKs of unsubstituted aromatic amines are near 3-4, the exact pK depending on the specific chemical environment and the temperature.

It is further required that the dye part possesses favorable absorbance (preferably higher then 450 nm) and emission wavelengths (preferably higher then 500 nm).

It is further required that the dye part is insensitive to notoric quenchers like oxygen. The latter is in particular not the case for oxygen-sensitive dyes (i.e., transition metal complexes).

As water-soluble dyes present in a hydrophilic matrix are generally easily washed out by aqueous samples, it is generally required to attach the dye to the matrix, most preferably by covalent linking. Dyes containing chemical groups for covalent attachment, i.e., via chemical reactions under mild ambient conditions are preferred.

Moreover, it is most advantageous that—within the pH range of interest—the dye part of a PET indicator dye is essentially insensitive to pH. Thus, for example, the fluorescein dye has a protonable group with a pK within the near neutral pH range.

Werner et al. (*Novel optical pH-sensor based on a borodiaza-indacene derivative*, FRESENIUS J. ANAL. CHEM. 359, 150-154 (1997)) describe a pH sensor based on a PET dye (1,3,5,7-tertramethyl-8-(4-dimethylamino)-4-difluorobora-3a,4a-diaza(s)-indacene) immobilized in a hydrogel matrix. The quencher group is dimethyl amino phenyl. The aromatic nitrogen reversibly reacts with protons. Due to its low pK (pK=3.3; see FIG. 3 in Werner et al., supra), the luminescence intensity of this indicator dye changes as a function of pH within the pH-range (~1.5-4.5). Accordingly, the dye is not useful for determination of physiol. pHs (i.e., blood).

Gareis et al. (*Phenol/phenolate-dependent on/off switching of the luminescence of 4,4-difluoro-4-bora-3a,4a-diaza-s-indacenes*, CHEM. COMMUN. 1717-1718 (1997)) reported that a 4-difluorobora-3a,4a-diaza(s)-indacene with a phenolic quencher group (PET donor group) shows a strong PET effect.

Wolfbeis et al., describe a number of PET dyes with —NR2 and —OH functional groups for determination of pH (see U.S. Pat. No. 6,001,999, col. 4, FIG. 2. and claim 8).

A titration of the dye (Gareis et al., supra) dissolved in $CHCl_3$ showed a strong decrease of the 520 nm emission band upon successive addition of pyridine. Gareis et al. embedded the dye in a hydrogel matrix of an optical sensor. In the matrix, the base form of the dye (phenolate species) showed low luminescence intensity, whereas the acid form of the indicator dye (phenol species) showed high luminescence intensity. From pH titration curves of the two phenols investigated, the pKs were determined to be 10.4 and 10.8, respectively.

SUMMARY OF THE INVENTION

It is against the above background that the present invention provides certain unobvious advantages and advancements over the prior art. In particular, the inventors have recognized a need for improvements in luminescent indicator dyes and optical sensors for the determination of near-neutral pH values in aqueous samples.

The state of the art suggests, that, due to their high pKs, PET dyes based on simple (mono- or bis hydroxy)phenols cannot be used as luminescent indicator dyes in optical sensors for determination of acidic and near neutral pHs. Furthermore, research conducted by the applicants shows that 4-difluorobora-3a,4a-diaza(s)-indacene dyes are not very stable when stored in aqueous solvents or water containing organic solvents for a longer period of time. Applicants' results suggest that 4-difluorobora-3a,4a-diaza(s)-indacene dyes are useful only in pH sensor applications not requiring exposure of the dye to a water containing environment for longer time periods (i.e., days).

PET dyes using the 4-aminonapthalimide luminophore as a dye part have been found to be particularly useful for optical $Na^+$, $K^+$, and $Ca^{++}$ sensors. Particularly for use in disposables carrying multiple optical sensors, it would be highly desirable to have a PET pH dye with spectral characteristics compatible with the "other" dyes.

None of the molecules with a phenolate donor group known from prior art can be used in practice for determination of pH in the physiological range (pH 6-8).

Although the present invention is not limited to specific advantages or functionality, it is noted that the present invention provides a luminescent dye suitable for measuring near neutral pH values in aqueous samples.

In accordance with one embodiment of the present invention, a compound having the general Formula I

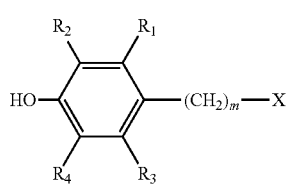

(I)

is provided, wherein
X is a luminophoric moiety,
m means the number 0, 1 or 2, and
$R_1$, $R_2$, $R_3$ and $R_4$ each independently represent hydrogen, chlorine or fluorine, with the proviso that at least one of $R_1$, $R_2$, $R_3$ and $R_4$ represent chlorine or fluorine.

A typical embodiment is characterized in that $R_2$ and/or $R_4$ represent chlorine or fluorine, and $R_1$ and $R_3$ represent hydrogen.

The luminophoric moiety X in the general Formula I in particular can be
(a) an amino-naphthalimide group of the general Formula II

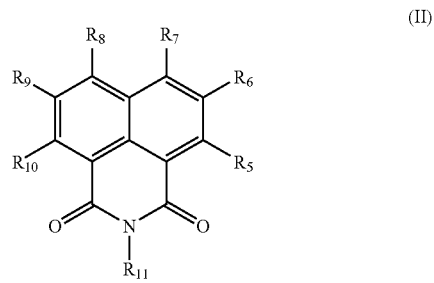

(II)

in which one of $R_5$, $R_6$, $R_7$, $R_8$, $R_9$ and $R_{10}$ is a group —NH— through which X is bound to the group —$(CH_2)_m$— of the compound mentioned in claim 1 of the general Formula I and the remainder and $R_{11}$ independently are hydrogen, a lipophilic or hydrophilic group or a reactive group for coupling to a polymer;
(b) a xanthenone group of the general Formula III

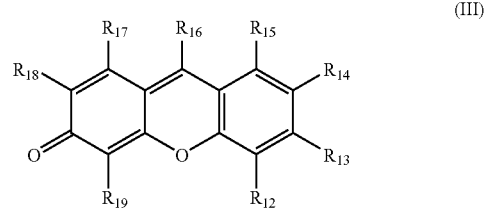

(III)

in which one of $R_{12}$, $R_{13}$, $R_{14}$, $R_{15}$, $R_{16}$, $R_{17}$, $R_{18}$, and $R_{19}$ represents a chemical bond through which X is bound directly (m=0) to the compound mentioned in claim 1 of the general Formula I and the remainder represent —OH, —$OR_{27}$, in which $R_{27}$ is a hydrophilic or a lipophilic group, —O—$R_{28}$-G, in which $R_{28}$ is a hydrophilic or a lipophilic group and G a reactive group for coupling to a polymer, or —$(CH_2)_n$—COOH, in which n is a number between 0 and 17, or group or a reactive group for coupling to a polymer; or
(c) a group of the general Formula IV

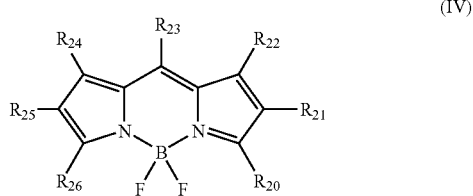

(IV)

in which one of $R_{20}$, $R_{21}$, $R_{22}$, $R_{23}$, $R_{24}$, $R_{25}$ and $R_{26}$ is a chemical bond through which X is bound to the group —$(CH_2)_m$— of the compound mentioned in claim 1 of the general Formula I and the remainder independently are hydrogen, a lipophilic or hydrophilic group or a reactive group for coupling to a polymer, or $R_{25}$ forms an aromatic ring system together with $R_{24}$ and $R_{21}$ forms an aromatic ring system together with $R_{22}$.

In accordance with another embodiment of the present invention, a compound of the formula

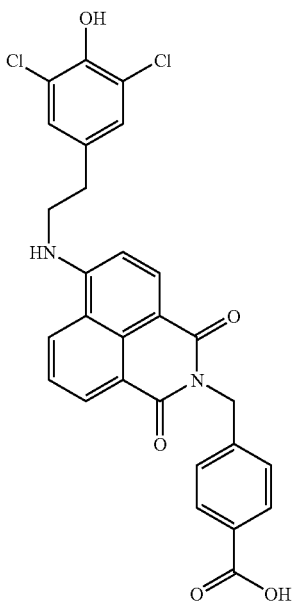

is provided.

In accordance with still another embodiment of the present invention, an optical sensor for determining the pH of aqueous media is provided comprising a luminescent dye, wherein the luminescent dye can be a compound according to one of the several embodiments of the present invention, and the compound is present in an immobilized form.

In accordance with yet another embodiment of the present invention, a method of determining the pH of aqueous media is provided comprising contacting an optical sensor according to one of the several embodiments of the present invention with the aqueous media. The aqueous media can be selected from blood, plasma or serum.

The inventive luminescent dyes show a dramatic change of their lumindecent behaviour in the pH range of between about 6.8 and about 8.0 and, in particular, in the pH range of between about 7.1 and about 7.6. Therefore, the inventive compounds can be used for the determination of a near neutral pH in an aqueous media, in particular blood, plasma or serum.

The luminescent dyes according to the general formulas mentioned above can be prepared by the skilled artisan by applying conventional synthetic methods (e.g., U.S. Pat. No. 6,124,135; U.S. Pat. No. 6,001,999). In the following, the invention will be described in greater detail by means of examples, wherein there will be explained the synthesis and properties of some preferred indicators. Other indicators in accordance with the present inventions can be prepared in analogous manner by the person skilled in the art.

These and other features and advantages of the present invention will be more fully understood from the following detailed description of the invention taken together with the accompanying claims. It is noted that the scope of the claims is defined by the recitations therein and not by the specific discussion of features and advantages set forth in the present description.

BRIEF DESCRIPTION OF THE DRAWINGS

The following detailed description of the embodiments of the present invention can be best understood when read in conjunction with the following drawings, where like structure is indicated with like reference numerals and in which.

Skilled artisans appreciate that elements in the figures are illustrated for simplicity and clarity and have not necessarily been drawn to scale. For example, the dimensions of some of the elements in the figures may be exaggerated relative to other elements to help improve understanding of the embodiment(s) of the present invention.

DETAILED DESCRIPTION OF THE INVENTION

In order that the invention may be more readily understood, reference is made to the following examples, which are intended to illustrate the invention, but not limit the scope thereof.

EXAMPLES

In the following, the chemical synthesis of a typical embodiment of the inventive dye (compound A41), its immobilization onto PVP beads, the preparation of optical sensor discs, and the pH measurement is described.

1. Synthesis of Dye A41

The luminescent dye A41 with the formula:

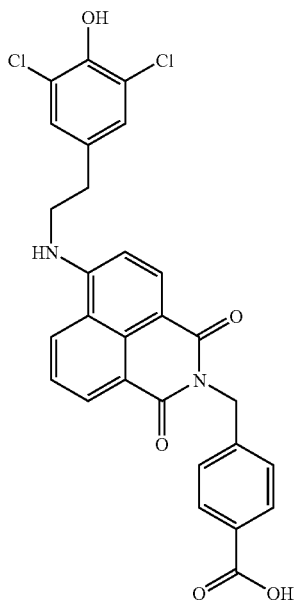

Chemicals
DCM (dichlormethane): Riedel de Haen 24233>99%
TFA (trifluoracetic acid): Fluka 91700>98%
NHS (N-hydroxysuccinimide): Fluka 56480>97%
DIC (diisopropylcarbodiimide): Fluka 38370>98%
DMAP (4-dimethylaminopyridine): Fluka 39405>98%
DIPEA (diisopropylethylamine): Fluka 03440>98%
acetonitrile: Merck-HPLC-grade
4-aminomethyl bencoic acid: Fluka: 08400>98%
$SOCl_2$: Fluka: 88950>99%
EtOH abs.: Riedel de Haen: 32221
TEA (triethylamine): Merck: 808352

SO$_2$Cl$_2$: Fluka: 862212
hydrazine-monohydrate: Fluka: 53850
phthalic anhydride: Fluka: 80020
tyramine hydrochloride: Fluka 93820>97%
NMP (N-methylpyrrolidone): Fluka: 69116
4-chloro-1,8-naphthalic anhydride: Aldrich: 19,149-3~95%

Figure 1A:
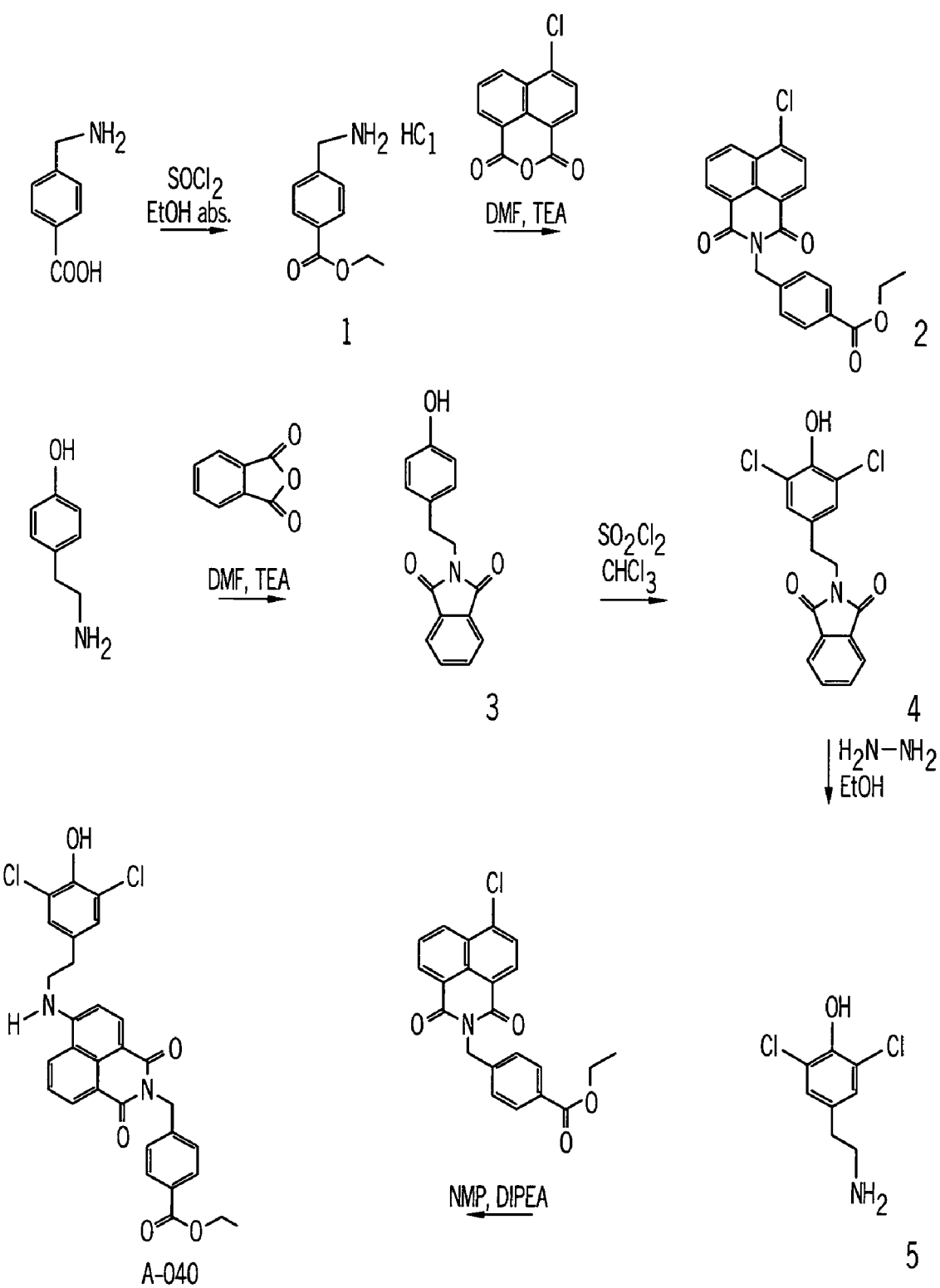
FIGS. 1a & 1b show the route of synthesis of a luminescent dye in accordance with one embodiment of the present invention.
Figure 1B:
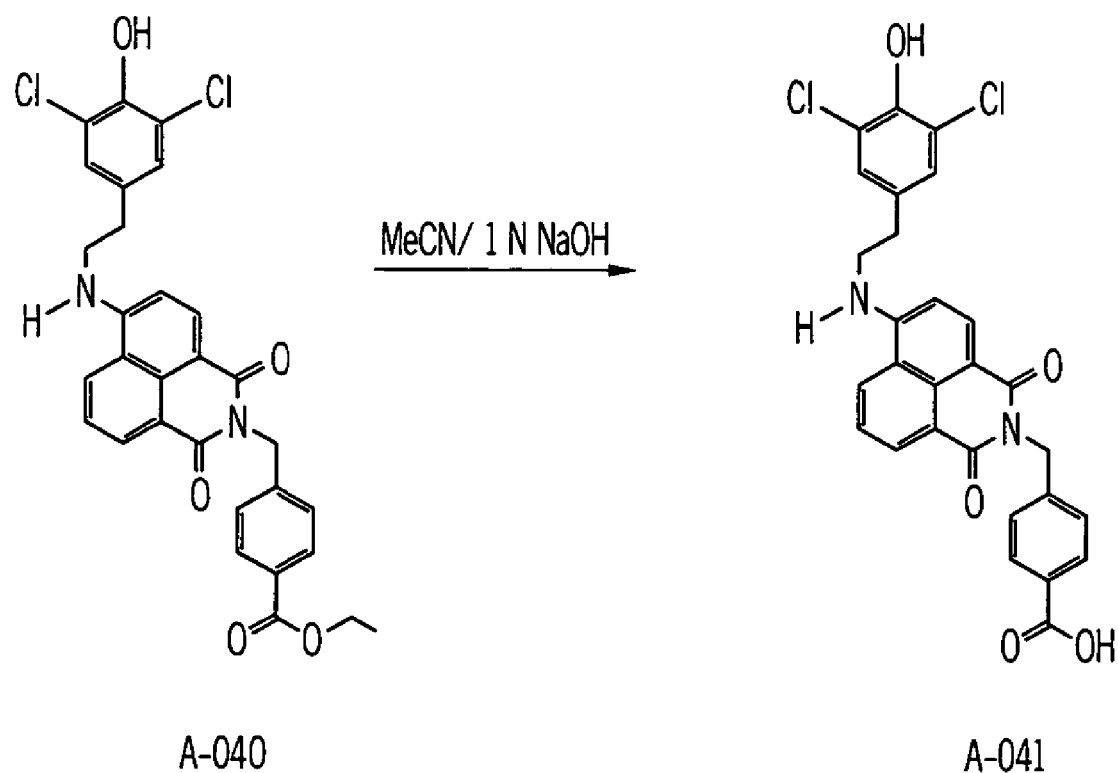

The synthetic route is shown in FIGS. 1a and 1b.

4-Aminomethylbencoic acid-ethylester hydrochloride (1): 20.0 g (132 mM) of 4-aminomethylbencoic acid were suspended in 200 ml EtOH abs. and cooled with ice. 28.0 g (17 ml) (236 mM) thionylchloride were added drop by drop. The clear mixture was then refluxed for 3 hours. After cooling to room temperature, EtOH was evaporated. 50 ml of toluene/EtOH 1/1 were added and evaporated three times. The residue was dried to get 27 g of 1.

4-Chloro-naphthalimidyl-methylbencoic acid-ethylester (2): 20.0 g (93.2 mM) 4-aminomethylbencoic acid-ethylester hydrochloride, 21.68 g (93.2 mM) 4-Chloro-1,8-naphthalic anhydride and 19.78 g triethylamine (195.5 mM) in 400 ml DMF were heated to 90° C. and stirred overnight.

After cooling to room temperature, 100 ml H$_2$O were added to precipitate the desired product.

The 4-Chloro-naphthalimidyl-methylbencoic acid-ethylester was recrystallized from EtOH. Yield: 15.8 g.

The HPLC (Vydac 10-90-15) shows a single peak at t=14.04 and the mass peak MH+=394.8 (M=393.82) was found in the Matrix Assisted Laser Desorption/Ionization Time-of-Flight (MALDI-TOF) mass spectrum.

Tyraminephthalimide (3): 29.6 g (200 mM) phthalic anhydride, 34.73 tyramine hydrochloride (200 mM) and 27.7 ml triethylamine (200 mM) were heated to 115° C. for 4 hours. After cooling to room temperature, the mixture was poured to 1.5 l icewater. The precipitate was filtered and washed with water. Yield: 45 g.

Dichlorotyraminephthalimide (4): 15.35 g (57 mM) tyraminphthalimide were added slowly and in portions to 24.75 g (170 mM) boiling sulfuryl chloride and 75 ml CHCl$_3$. Refluxing was continued till the mixture became clear. Then the solution was stirred openly at room temperature overnight to remove sulfuryl chloride. The solvent was removed by evaporation and the crude product was recrystallized from 75 ml MeOH. Yield: 7.2 g.

Dichlorotyramine (5): 7.2 g dichlorotyraminephthalimide and 1.6 ml hydrazine monohydrate were refluxed in 170 ml EtOH abs. overnight. After cooling to room temperature, the precipitate was filtered off. The crude product was not purified for further synthesis.

A-040: A mixture of 1.5 g (7.26 mM) dichlorotyramine, 2.85 g 4-chloronaphthalimidylmethylbenzoic acid ethylester and 4 ml DIPEA in 150 ml NMP was heated to 90° C. for 4 days.

After cooling to room temperature, 1.5 l water and 7 ml AcOH were added. The precipitate was filtered off and dissolved in 400 ml CHCl$_3$. The organic layer was extracted with 0.5 N NaOH three times and the NaOH-layer was acidified with 6N HCl. The water layer was extracted with ethyl acetate and the organic layer containing the dye was dried over MgSO$_4$. Solvent was removed by evaporation. Finally the crude A-040 was purified via dry flash silica gel column chromatography.

Gradient: petrolether
petrolether/ethyl acetate 9/1
petrolether/ethyl acetate 8/2
petrolether/ethyl acetate 7/3
petrolether/ethyl acetate 1/1

The HPLC (Vydac: 10-90-15) shows a single peak at t=13.42 min and the mass peak M=563 (M=563) was found by MALDI-TOF measurement.

A-041: A-040 was dissolved in 50 ml acetonitrile and 50 ml 1N NaOH. The solution was warmed up to 60° C. and stirred for 1 hour. Then the solution was acidified with HCl and extracted with ethyl acetate. The ethyl acetate layer containing the dye was washed with water three times. After drying the organic layer over MgSO$_4$, the solvent was removed by evaporation. Yield: 350 mg.

The HPLC (Vydac: 10-90-15) shows a single peak at t=11.3 min and the mass peak MH+=535.4 (M=534.4) was found by MALDI-TOF measurement.

2. Synthesis of Polyvinylpyrrolidon (PVP) Beads

The following synthetic scheme was applied:

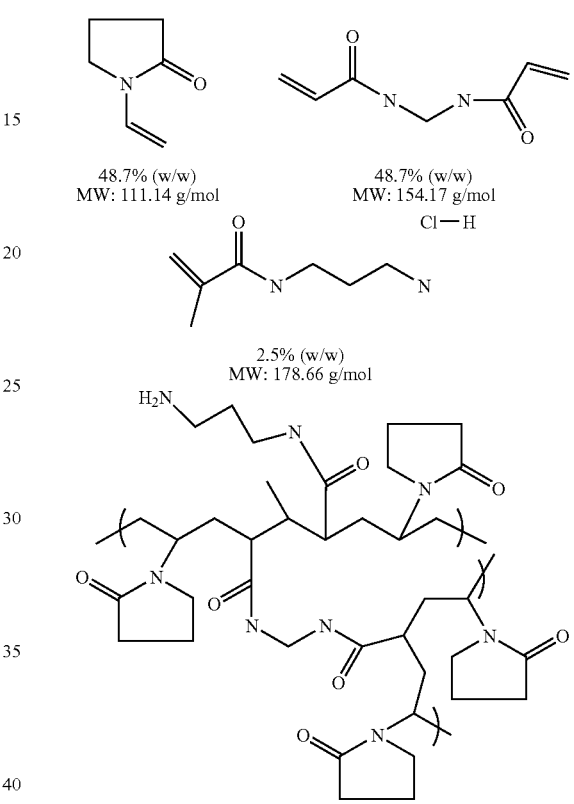

400 gram deaerated, de-ionized water are added into a 500 ml round bottom flask with a nitrogen inlet. The flask is equipped with a magnetic stirring bar (size: 7 mm diameter, 40 mm length) and a reflux condenser and placed in a oil bath at a temperature of 70+/−2° C. A Teflon® (polytetrafluorethylene) tightening is used to connect the flask and the condenser to avoid gluing of the condenser to the flask. Under vigorous stirring and a slight nitrogen stream, stirring is continued for 45 min to ensure the removement of oxygen. 10 g of Methylen-Bisacrylamid (Fluka 66667) and 500 mg N-Amino-Propyl-methacrylamide (Polysciences 21200) are added in one portion. 10 ml of Vinylpyrolidon (Aldrich, V340-9) are added in one portion afterwards. Stirring is continued under a slight nitrogen stream for 15 min.

800 mg of Ammoniumperoxodisulfate (Fluka, 09920) are dissolved in 10 ml bidest water and added immediately after complete dissolving to the reaction solution (usually a lot of air bubbles are formed during dissolving, but one should not wait with the addition of the solution until the air bubbles disappeared). Stirring and heating under slight nitrogen stream is to be continued until a slight opalescence occurs (usually after a few minutes). Nitrogen is switched off and stirring and heating is continued for 2 hours. After 30 min to 1 h the reaction mixture gets semisolid and stirring is not possible anymore.

The reaction mixture is diluted with approximately 500 ml water and filtered of with a "Büchner"—funnel 15 cm diameter, using a paper filter (Schleicher&Schüll, Nr.589[1], Schwarzband, fast filtration). The precipitate is resuspended in 1 l water (2 l beaker, stirring bar size: 10 mm diameter, 80 mm length) and stirred for at least 4 h and filtered off again. This washing procedure is repeated 5 times (at least one of the stirring times is extended over night). Afterwards it is resuspended in 500 ml 99% Ethanol, stirred for at least 2 h and filtered off again. This procedure is repeated three times. The product is dried in an exciscator under vacuum.

More easily redispersable particles may be obtained with different drying conditions: freeze drying usually yields a fine powder.

3. Immobilization of Dye A41 onto the PVP Beads

The following synthetic scheme was applied:

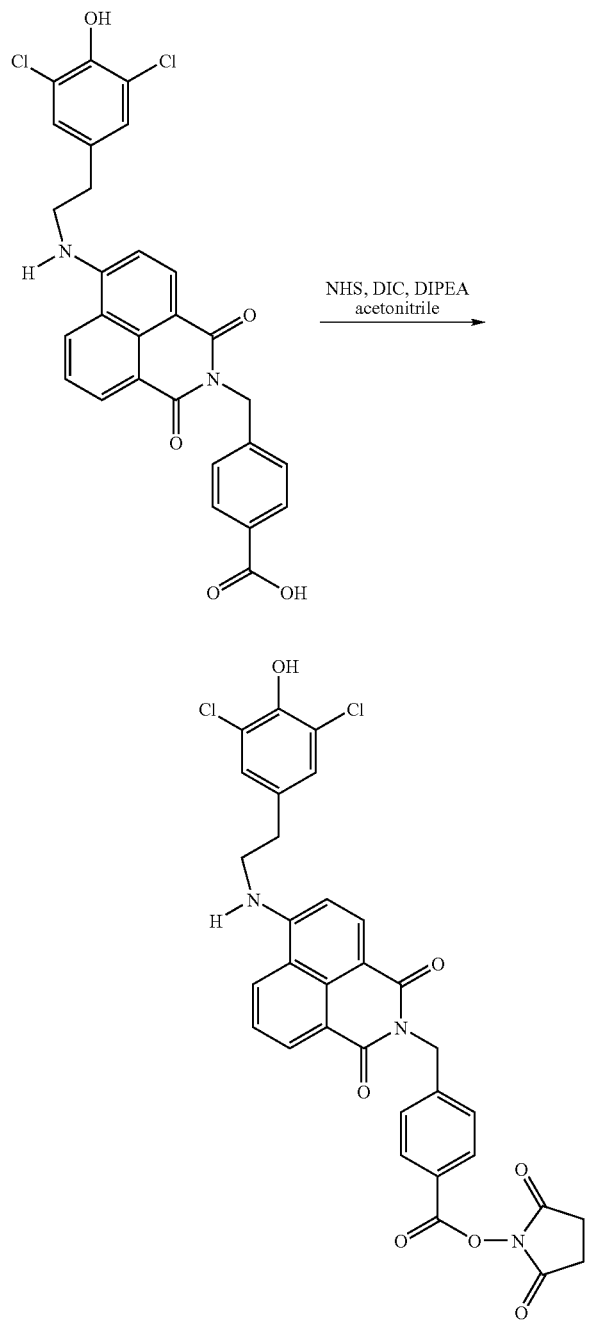

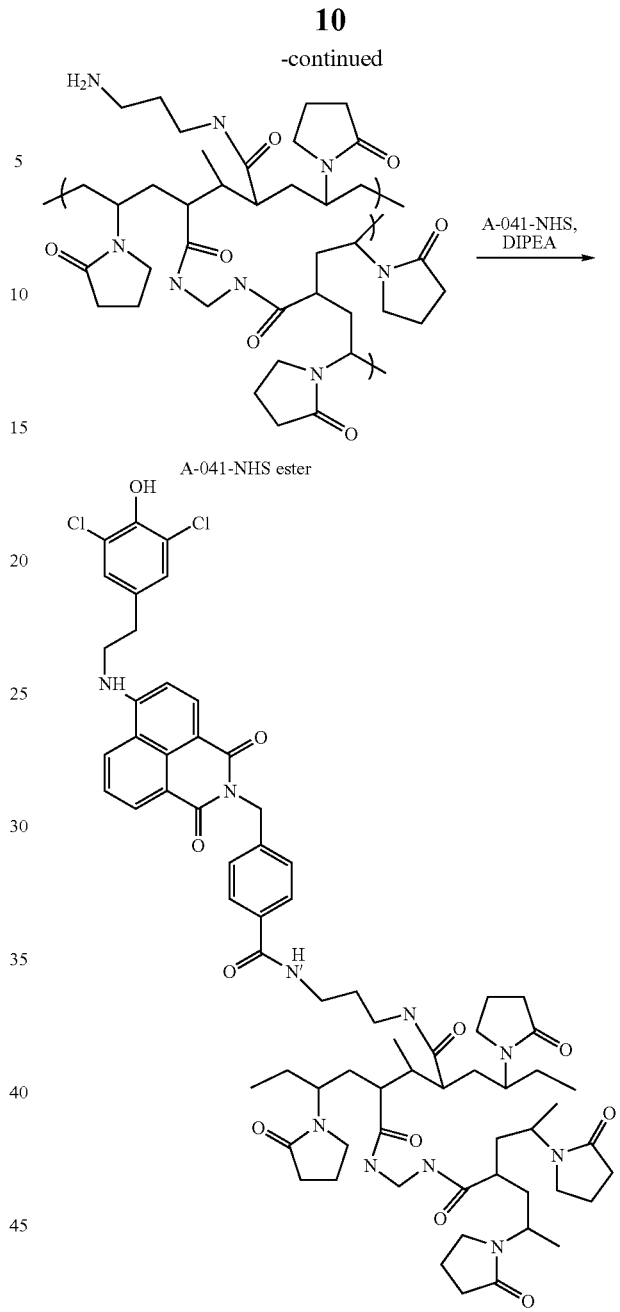

60 mg A-041, 20 mg NHS, 20 mg DIC and a catalytical amount of DMAP were stirred at room temperature in 2 ml DMF and 20 ml acetonitrile for 3 hours.

After this period the HPLC shows that the NHS-ester of the NaFI was formed quantitatively.

HPLC (Vydac: 10-90-15V4.M, 215/430 nm) single peak at t=12.1 min.

A41-coupling on PVP beads: 400 mg PVP were weaked in 20 ml water for 4 hours at room temperature, before the solution of the NaFI—NHS ester in acetonitrile (see above) and 1 ml DIPEA were added.

The suspension was allowed to stir at room temperature for 3 days. Then the suspension was centrifugated and the liquid was poured off. The pellet was washed with acetonitrile till the liquid was colourless and the stench of DIPEA disappeared.

After this procedure the dye loaded PVP beads were dried in an exciccator.

4. Preparation of the Casting Solutions
   Components of Casting Solutions:
   dye loaded PVP beads
   Hydrophilic polyether-polyurethane, water uptake 50% (Cardiotech International, 78 E Olympia Avenue, Woburn, Mass. 01801-2057, USA)
   ethanol:water, 90:10, v/v
   carbon black (Flammruβ 101, Degussa)
   Indicator layer casting solution: 100 mg of the dye loaded PVP beads were suspended in 4.75 ml ethanol:water till they were homogenous distributed. Then the polyether-polyurethane hydrogel was added and the mixture was stirred overnight.
   Overcoat layer casting solution: 1 g hydrogel was dissolved in 9 g ethanol:water. 0.3 g carbon black were added and dispersion was stirred for 14 h at room temperature.

5. Preparation of Optical Sensors Disks
   The indicator layer casting solution was coated onto a polyester foil (Melinex foil, ICI America) and the solvent was evaporated. The final dry thickness of the indicator layer was approximately 10 μm. Then, the overcoat layer casting solution was coated onto the indicator layer and the solvent was evaporated. The final a dry thickness of the overcoat layer was about 5 μm. Then, a small sensor disc (2.5 cm diameter) was punched out and soaked in buffer for at least 17 h for activation.
   Methods of cutting and measuring sensor discs are described by M. J. P. Leiner and P. Hartmann, *Theory and Practice in optical pH sensing*, in SENSORS AND ACTUATORS, B 11, 281-289 (1993), and by M. J. P. Leiner in ANALYTICA CHIMICA ACTA 255, 209-222 (1991).

6. Preparation of pH Buffer Solutions
   Solution A (0.02 mol/L HCL 0.146 mol/L NaCl)
   Solution B (0.05 mol/L TRIS-HCl 0.146 mol/L NaCl)
   Aliquots of solutions A and B were mixed in appropriate rations to obtain eleven pH buffer solutions of pH 2.67, 3.66, 5.41, 6.35, 6.74, 7.28, 7.76, 8.29, 8.78, 9.81, 10.79, respectively. The pHs were determined at 37° C. with a standard glass electrode.

Figure 2:
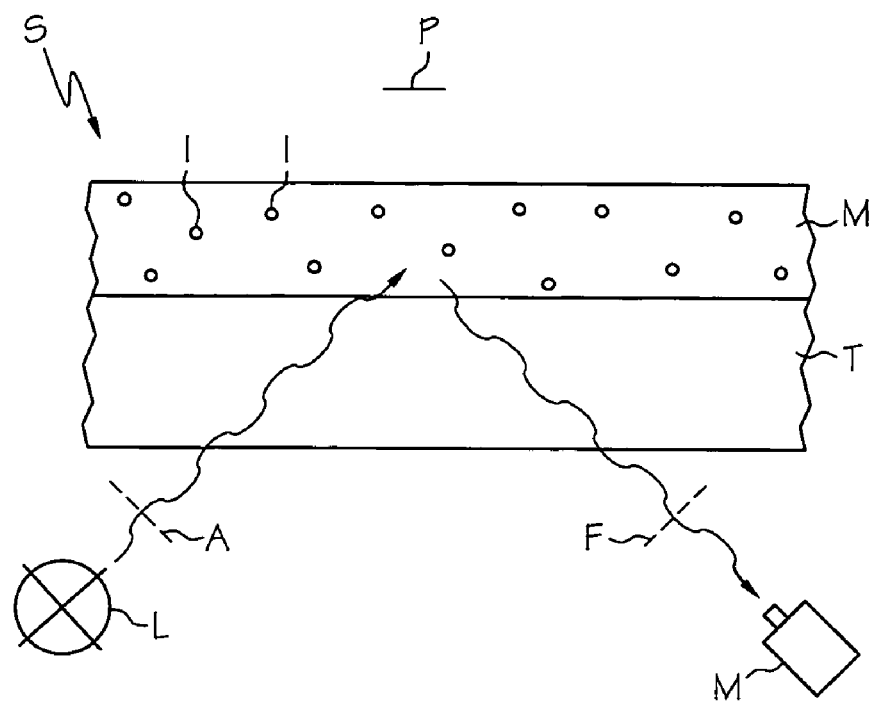
FIG. 2 is a partial view, shown in cross section, of a sensor disk that can be employed in accordance with at least one embodiment of the present invention.

7. Measurement
   The sensor discs thus obtained were used in the measuring set-up represented schematically in FIG. 2. In FIG. 2, the reference character S denotes a portion of the sensor disc. The compound of the invention suspended in the hydrophilic ion-permeable polymer (hydrogel) and immobilized on PVP beads is denoted by I. This layer M is carried by a substrate T permeable to excitation and measuring radiation, which is a transparent material.
   According to the invention, the compound I of the invention can be bound to the ion-permeable matrix directly in a covalent manner or it can be present in the matrix or in the sample in physically dissolved condition.
   For measurement, the sensor disc was introduced into a thermostatted (37° C.) flow-through cell impervious to light and was contacted with samples P (=buffer solutions) having different pHs.
   The optical measuring system consisted of a blue LED as the light source L, a photodiode M as the detector, optical filters A and F for selecting the wavelengths, a fiber-optic arrangement for conducting the excitation light into the polymer M and for conducting the emission light to the photodetector M as well as a device for electronic signal processing (not illustrated). At the excitation end there was utilized an interference filter (peak transmission at 480 nm) and at the emission end a 520 nm cut-off filter.

Figure 3:
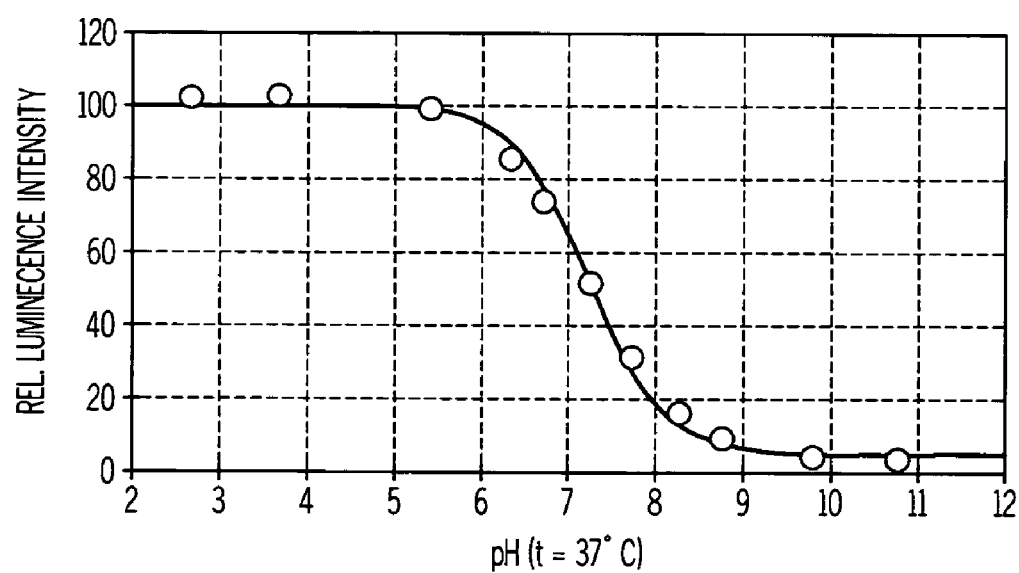
FIG. 3 is a plot showing the relative luminescence intensity (ordinate) of A41 of the present invention, immobilized on PVP beads dispersed in a hydrophilic polymer layer, as a function of various pHs.

8. Results
   FIG. 3 shows the relative luminescence intensity (ordinate) of A41 of the invention, immobilized on PVP beads dispersed in a hydrophilic polymer layer, as a function of various pHs. The data in FIG. 3 are scaled to yield a maximum intensity value of 100.

The intensity data (circles in FIG. 3) were fitted to the following equation using a commercially available least squares regression algorithm.

$$L = L_m \left( 1 + \frac{q - 1}{1 - 10^{pH - pK}} \right)$$

L denotes luminescence intensity and $L_m$ denotes maximum luminescence intensity. The algorithm returned a pK value of 7.25 and a q value of 0.05. The latter means that the "OFF" intensity is 5% of the "ON" intensity. (ON intensity=luminescence intensity of the protonated species (i.e., in FIG. 3 the intensity at pHs<5), OFF intensity=intensity of the deprotonated species (i.e., in FIG. 3 the intensity at pHs>10).

The example demonstrates that the compound according to the invention can be used for determination of near neutral pHs.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the invention in detail and by reference to specific embodiments thereof, it will be apparent that modifications and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

What is claimed is:

1. A compound having the general Formula I

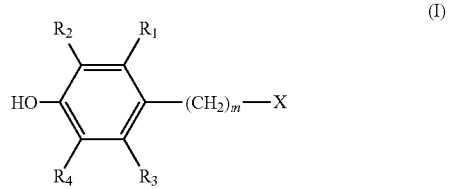

(I)

wherein
   X is a luminophoric moiety, wherein the luminophoric moiety X is an amino-naphthalimide group of the general Formula II

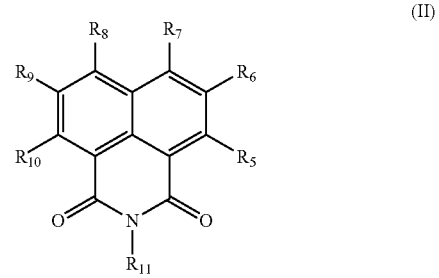

(II)

in which one of $R_5$, $R_6$, $R_7$, $R_8$, $R_9$ and $R_{10}$ is a group —NH— through which X is bound to the group —$(CH_2)_m$— and the remainder and $R_{11}$ independently are hydrogen, a lipophilic or hydrophilic group or a reactive group for coupling to a polymer;

m means the number 0, 1 or 2; and $R_1$, $R_2$, $R_3$ and $R_4$ each independently represent hydrogen, chlorine or fluorine, with the proviso that at least one of $R_1$, $R_2$, $R_3$ and $R_4$ represent chlorine or fluorine.

2. The compound of claim 1, wherein $R_2$ and/or $R_4$ represent chlorine or fluorine, and $R_1$ and $R_3$ represent hydrogen.

3. A compound of the formula

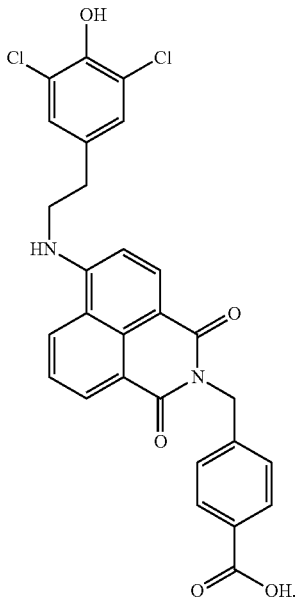

4. An optical sensor for determining the pH of aqueous media comprising a luminescent dye and a matrix, wherein said luminescent dye is a compound according to claim 1, and said luminescent dye is immobilized to said matrix.

5. An optical sensor for determining the pH of aqueous media comprising a luminescent dye and a matrix, wherein said luminescent dye is a compound according to claim 2, and said luminescent dye is immobilized to said matrix.

6. An optical sensor for determining the pH of aqueous media comprising a luminescent dye and a matrix, wherein said luminescent dye is a compound according to claim 3, and said luminescent dye is immobilized to said matrix.

7. A method of determining the pH of aqueous media comprising contacting an optical sensor according to claim 4 with said aqueous media.

8. The method of claim 7, wherein said aqueous media is selected from blood, plasma or serum.

9. A method of determining the pH of aqueous media comprising contacting an optical sensor according to claim 5 with said aqueous media.

10. The method of claim 9, wherein said aqueous media is selected from blood, plasma or serum.

11. A method of determining the pH of aqueous media comprising contacting an optical sensor according to claim 6 with said aqueous media.

12. The method of claim 11, wherein said aqueous media is selected from blood, plasma or serum.

\* \* \* \* \*

UNITED STATES PATENT AND TRADEMARK OFFICE
CERTIFICATE OF CORRECTION

| | | |
|---|---|---|
| PATENT NO. | : 8,097,725 B2 | Page 1 of 1 |
| APPLICATION NO. | : 11/003163 | |
| DATED | : January 17, 2012 | |
| INVENTOR(S) | : Huarui He et al. | |

It is certified that error appears in the above-identified patent and that said Letters Patent is hereby corrected as shown below:

Col. 1, Line 45, "PERKN" should read --PERKIN--

Col. 2, Lines 24-25, "higher then" should read --higher than--

Col. 7, Line 4, "Fluka 93820" should read --Fluka: 93820--

Col. 8, Line 67, "filtered of with a" should read --filtered with a--

Col. 11, Line 22, "The final a dry" should read --The final dry--

Signed and Sealed this
Tenth Day of July, 2012

David J. Kappos
*Director of the United States Patent and Trademark Office*